United States Patent
Vogler et al.

(10) Patent No.: US 9,655,514 B2
(45) Date of Patent: May 23, 2017

(54) OPTICAL INSTRUMENT FOR BIOMECHANICAL DIAGNOSIS OF EYE DISEASE

(71) Applicant: Wavelight GmbH, Erlangen (DE)

(72) Inventors: Klaus Vogler, Blankenhain (DE); Christian Wuellner, Erlangen (DE)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 15/008,206

(22) Filed: Jan. 27, 2016

(65) Prior Publication Data

US 2016/0220110 A1 Aug. 4, 2016

(30) Foreign Application Priority Data

Feb. 2, 2015 (WO) ................. PCT/EP2015/052079

(51) Int. Cl.
| | |
|---|---|
| *A61B 3/14* | (2006.01) |
| *A61B 3/10* | (2006.01) |
| *A61B 5/00* | (2006.01) |
| *G01N 21/63* | (2006.01) |
| *A61B 3/107* | (2006.01) |

(52) U.S. Cl.
CPC .......... *A61B 3/1025* (2013.01); *A61B 3/1005* (2013.01); *A61B 3/107* (2013.01); *A61B 5/0075* (2013.01); *G01N 21/636* (2013.01); *G01N 2021/638* (2013.01)

(58) Field of Classification Search
USPC ....................................................... 351/206
See application file for complete search history.

(56) References Cited

U.S. PATENT DOCUMENTS

| | | |
|---|---|---|
| 6,795,199 B2 | 9/2004 | Suhami |
| 2005/0140982 A1 | 6/2005 | Chen et al. |
| 2014/0367579 A1 | 12/2014 | Otsuka |

FOREIGN PATENT DOCUMENTS

WO 2012/149570 A1 11/2012

*Primary Examiner* — Jack Dinh

(57) ABSTRACT

A method and system for performing biomechanical diagnosis of eye disease may include a Brillouin light source to generate a Brillouin sample beam, and a second harmonic generation (SHG) light source to generate an SHG sample beam. Both the Brillouin sample beam and the SHG sample beam may be coincidentally directed to a biological tissue sample in a confocal manner to a focus position. Brillouin scattering resulting from the Brillouin sample beam may be detected to determine an elastomechanical property and a viscoelastic property of the sample. SHG scattering resulting from the SHG sample beam may be detected to determine an indication of a morphological structure of the sample. The sample may be an in vivo human cornea.

18 Claims, 4 Drawing Sheets

300 — METHOD FOR BIOMECHANICAL DIAGNOSIS OF EYE DISEASE

VARY AN AXIAL POSITION OF THE FOCUS POSITION WITHIN THE BIOLOGICAL TISSUE SAMPLE ALONG A FIRST AXIS PARALLEL TO THE FIRST SAMPLE BEAM AND THE SECOND SAMPLE BEAM — 302

VARY A LATERAL POSITION OF THE FOCUS POSITION WITHIN THE BIOLOGICAL TISSUE SAMPLE ALONG AT LEAST ONE OF A SECOND AXIS AND A THIRD AXIS THAT ARE PERPENDICULAR TO THE FIRST AXIS — 304

SCAN THE BIOLOGICAL TISSUE SAMPLE TO GENERATE IMAGE DATA USING THE SECOND SIGNAL BEAM, SUCH THAT BOTH THE FIRST SAMPLE BEAM AND THE SECOND SAMPLE BEAM ARE DIRECTED TO DIFFERENT COMMON POSITIONS AT THE BIOLOGICAL TISSUE SAMPLE, AND INCLUDING VARYING AT LEAST ONE OF THE AXIAL POSITION OF THE FOCUS POSITION AND THE LATERAL POSITION OF THE FOCUS POSITION — 306

FIG. 3

OPTICAL INSTRUMENT FOR BIOMECHANICAL DIAGNOSIS OF EYE DISEASE

CROSS REFERENCE TO RELATED APPLICATIONS

This application claims priority to International Application Serial Number PCT/EP2015/052079, filed 2 Feb. 2015, titled "OPTICAL INSTRUMENT FOR BIOMECHANICAL DIAGNOSIS OF EYE DISEASE," which is hereby incorporated by reference in its entirety.

BACKGROUND

Field of the Disclosure

The present disclosure relates to spectroscopic instruments and methods, and more specifically, to an optical instrument for biomechanical diagnosis of eye disease.

Description of the Related Art

Various diagnostic and clinical instruments have been developed for in vivo imaging of biological issues, and in particular, for imaging structures in a human eye. Specifically, optical instruments are used to measure geometrical and optical characteristics of different sections of the human eye. The geometric and optical characteristics provided by such analyses may enable various degrees of biomechanical or physiological modelling of an individual eye of a patient in an effort to diagnose an ophthalmological health condition and to develop a suitable treatment plan.

Keratoconus is a degenerative disease of the human eye, which is characterized by a noninflammatory thinning and steepening of the curvature in the central or paracentral cornea, resulting in a conical cornea that characterizes the disease. The structural changes in the cornea as keratoconus progresses cause significant impairment of vision in a patient. Structural changes of the cornea caused by keratoconus may further complicate certain laser vision correction surgeries, such as laser assisted in situ keratomileusis (LASIK) surgery or photorefractive keratectomy (PRK) surgery, because of possible increased risks from post-surgical corneal ectasia (or thinning).

The visual impairment caused by keratoconus may be corrected to a degree using specially adapted eyeglasses or corneoscleral contact lenses. Such measures, however, may not be effective when keratoconus advances to a late stage of pathogenesis. For advanced stage keratoconus, a corneal crosslinking treatment is performed, which may stop or at least decelerate pathogenesis, although complete visual rehabilitation is not presently prognosticated.

Besides keratoconus, other types of corneal degeneration may impact the biomechanical stability of the human cornea. For example, pellucid marginal corneal degeneration (PMD), which is also known as keratotorus, is a degenerative noninflammatory corneal condition, which is typically characterized by a clear, bilateral ectasia in the inferior and peripheral region of the cornea. In particular, patients with PMD may exhibit normal thickness in the center of the cornea with an intact central epithelium, while exhibiting a peripheral band of thinning in the inferior cornea. The portion of the cornea that is immediately adjacent to the limbus may be spared by PMD, and typically includes a strip of about a few millimeters. As a further result of PMD, Bowman's layer of the cornea may be absent, irregular, or may have ruptured areas.

Optical examinations of the viscoelastic properties of eye tissues, such as the cornea and the eye lens, have been performed using Brillouin scattering (BS), which relies on position-dependent mass density variations inside a sampled material to scatter incident coherent light by means of a phonon-photon interaction. By spectroscopically analyzing a Brillouin scattered light beam from eye tissue, certain biomechanical properties of the eye tissue may be determined, such as a viscoelastic property of the analyzed eye tissue. The determination of the viscoelastic properties of eye tissue using Brillouin scattering may be particularly useful in connection with keratoconus crosslinking treatments of the cornea using ultraviolet (UV) light, in order to probe and document an actual qualitative impact of the crosslinking treatment on relevant biomechanical properties of the cornea, such as hardness and stiffness.

Furthermore, the fine biostructure of the cornea may be examined using multiphoton microscopy to generate certain images of eye tissue. During multiphoton imaging, different structures in the cornea are excited through multiphoton absorption and may undergo autofluorescence. Alternatively, certain non-isotropic structures, such as collagen fibrils in the cornea, may used for second harmonic generation (SHG) or third harmonic generation (THG) of wavelengths of a sample beam through non-linear interaction. In this manner, SHG or THG signals may indicate the position and distribution of various structures in the cornea.

In particular, SHG signals have been associated with the position and distribution of the fibrils in the cornea. The arrangement and orientation of corneal fibrils, as well as their position and density, may correlate with the optical and the mechanical properties of the cornea in the regions analyzed using SHG signals. The optical properties may include transparency and scattering, while the mechanical properties may include elastomechanical properties, such as strength. It is known that in advanced stages of eye diseases, such as keratoconus and corneal dystrophy, changes in the optical and mechanical properties of affected eye tissue are detectable in the coarse structure of the cornea. Therefore, analysis using SHG signals may be a suitable method to examine the fine structure of the cornea and may enable early detection of the pathogenesis of eye disease. Additionally, SHG signals are generated in vivo from corneal fibrils during certain LASIK surgeries with femtosecond (fs) lasers and may provide insight into directionality and position of LASIK incisions.

SUMMARY

In one aspect, a disclosed method for performing biomechanical diagnosis of eye disease includes generating a first sample beam and a second sample beam sharing an optical start point and propagating the first sample beam and the second sample beam to a biological tissue sample in a confocal manner to a focus position at the biological tissue sample. The method includes detecting a first signal beam comprising first photons backscattered by the first sample beam from the focus position. The first signal beam is detected using a Brillouin scattering detector. The method also includes detecting a second signal beam comprising second photons backscattered by the second sample beam from the focus position. The second signal beam is detected using a second harmonic generation (SHG) detector.

In any of the disclosed embodiments, the method may further include determining, from the first signal beam, an elastomechanical property of the biological tissue sample at the focus position, determining, from the first signal beam, a viscoelastic property of the biological tissue sample at the focus position, and determining, from the second signal beam, an indication of a morphological structure of the biological tissue sample at the focus position.

In any of the disclosed embodiments of the method, propagating the first sample beam and the second sample beam to the sample in the confocal manner may include propagating the first sample beam and the second sample beam along a common optical path.

In any of the disclosed embodiments of the method, the first sample beam may be generated using a narrow band continuous wave laser, the second sample beam may be generated using a femtosecond-fiber laser, the Brillouin scattering detector may include a spectrometer, and the SHG detector may include a photocathode sensitive to the second signal beam.

In any of the disclosed embodiments of the method, the first signal beam may include Rayleigh scattered photons and Brillouin scattered photons from the focus position, while the second signal beam may include photons at a half-wavelength of a wavelength of the second sample beam. In any of the disclosed embodiments of the method, the biological tissue sample may be in vivo biological tissue comprising a portion of a human eye.

In any of the disclosed embodiments of the method, propagating the first sample beam and the second sample beam to the sample in the confocal manner may include varying an axial position of the focus position within the biological tissue sample along a first axis parallel to the first sample beam and the second sample beam. In any of the disclosed embodiments of the method, propagating the first sample beam and the second sample beam to the sample in the confocal manner may include varying a lateral position of the focus position within the biological tissue sample along at least one of a second axis and a third axis that are perpendicular to the first axis. In any of the disclosed embodiments of the method, propagating the first sample beam and the second sample beam to the sample in the confocal manner may include scanning the biological tissue sample to generate image data using the second signal beam. In the method, the first sample beam and the second sample beam may be directed to different common positions at the biological tissue sample. In the method, the scanning may include varying at least one of the axial position of the focus position and the lateral position of the focus position.

In another disclosed aspect, an optical instrument for performing biomechanical diagnosis of eye disease includes a first light source to generate a first sample beam, and a second light source to generate a second sample beam. The optical instrument further includes a first partial mirror to superimpose the first sample beam and the second sample beam to generate a combined sample beam. The optical instrument also includes a Brillouin scattering detector including a spectrometer to receive a first signal beam comprising first photons backscattered by the first sample beam from a focus position at a biological tissue sample. The optical instrument still further includes a second harmonic generation (SHG) detector including a photocathode sensitive to a second signal beam comprising second photons backscattered by the second sample beam from the focus position.

In any of the disclosed embodiments, the optical instrument may further include a second partial mirror to propagate the combined sample beam to the focus position in a confocal manner, and propagate a combined signal beam comprising the first signal beam and the second signal beam from the focus position in a confocal manner.

In any of the disclosed embodiments, the optical instrument may further include a focusing element to vary an axial position of the focus position at the biological tissue sample in a confocal manner along a first axis parallel to the combined sample beam. In any of the disclosed embodiments, the optical instrument may further include a scanning element to vary a lateral position of the focus position at the biological tissue sample in a confocal manner along at least one of a second axis and a third axis that are perpendicular to the first axis. In the optical instrument, at least one of the focusing element and the scanning element may be to scan the biological tissue sample to generate image data using the second signal beam. In the optical instrument, both the first sample beam and the second sample beam may be directed to different common positions at the biological tissue sample. In the optical instrument, at least one of the focusing element and the scanning element may be to vary at least one of the axial position of the focus position and the lateral position of the focus position.

In any of the disclosed embodiments of the optical instrument, the first light source may include a narrow band continuous wave laser, the second light source may include a femtosecond-fiber laser, the Brillouin scattering detector may include a spectrometer, and the SHG detector may include a photocathode sensitive to the second signal beam.

In any of the disclosed embodiments of the optical instrument, the first signal beam may include Rayleigh scattered photons and Brillouin scattered photons from the focus position, while the second signal beam may include photons at a half-wavelength of a wavelength of the second sample beam. In the optical instrument, the biological tissue sample may be in vivo biological tissue comprising a portion of a human eye.

In any of the disclosed embodiments of the optical instrument, the Brillouin scattering detector may be to determine, from the first signal beam, an elastomechanical property of the biological tissue at the focus position, and determine, from the first signal beam, a viscoelastic property of the biological tissue at the focus position. In any of the disclosed embodiments of the optical instrument, the SHG detector may be to determine, from the second signal beam, an indication of a morphological structure of the biological tissue sample at the focus position.

BRIEF DESCRIPTION OF THE DRAWINGS

For a more complete understanding of the present invention and its features and advantages, reference is now made to the following description, taken in conjunction with the accompanying drawings, in which:

FIG. 3 is a flow chart of selected elements of a method for biomechanical diagnosis of eye disease.

DESCRIPTION OF PARTICULAR EMBODIMENT

Figure 1:
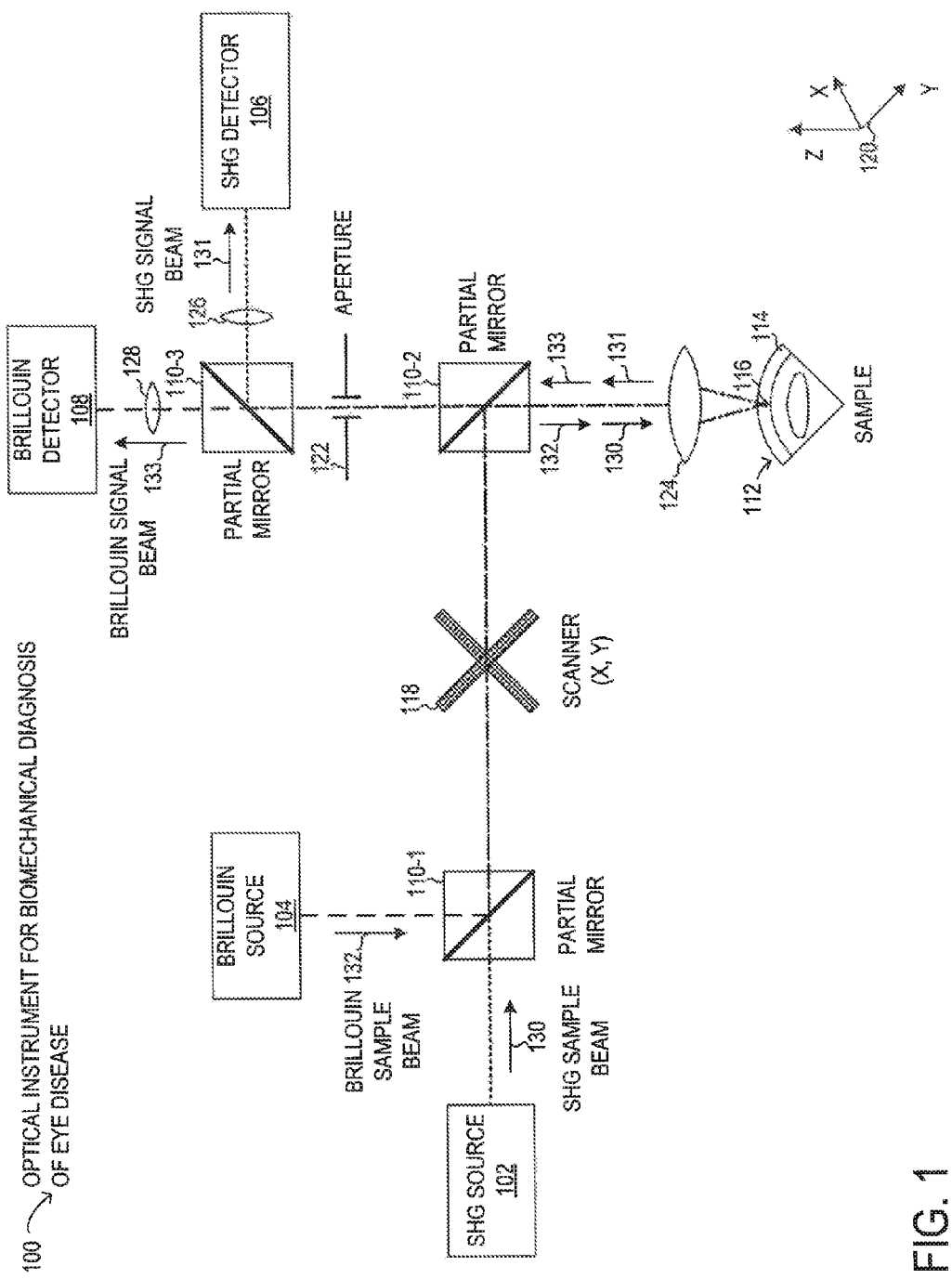
FIG. 1 is a block diagram of selected elements of an embodiment of an optical instrument for biomechanical diagnosis of eye disease.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

For early detection eye disease resulting in corneal degeneration impacting the biomechanical stability of the human cornea, such as keratoconus, it may be desirable to physically analyze the cornea using optical examination methods that are suitable for reliable diagnosis of the onset of pathogenesis of various eye diseases. Desirable optical examination methods may enable detection corneal degeneration before clinically manifested macroscopic structural changes of the cornea emerge.

Typically, different methods for optical examination of eye tissue, such as Brillouin scattering and multiphoton imaging, are performed separately in a spatially uncorrelated manner with respect to the structures in the eye tissue. The separate optical examination methods may be a constraining factor in better understanding and characterizing the physical properties of eye tissue in many diagnostic and clinical applications.

Thus, different and spatially uncorrelated optical examination methods may limit the analysis and characterization of structures in eye tissue in many diagnostic and clinical applications. In the following description, an optical system for biomechanical eye disease is disclosed that may attain a spatially precise correlation of a Brillouin scattering signal and an SHG signal from eye tissue, including the human cornea.

The cornea, or individual structural portions of the cornea, may be characterized as a linear-elastic, homogeneous or isotropic material. The biostructure of the cornea includes the conical epithelium, Bowman's layer (also known as the anterior limiting membrane), the corneal stroma (also known as substantia propria), Dua's Layer, Descemet's membrane (also known as posterior limiting membrane) and the corneal endothelium. For the etiology and during the pathogenesis of corneal eye disease, changes of the biomechanical properties of the cornea may be considered highly relevant to detecting the eye disease.

A biomechanical property of a material, such as the human cornea, may be represented by an elastomechanical property or a viscoelastic property or a combination thereof, and may be related to stiffness of the material. Biomechanical properties may be characterized using different moduli.

Stress may be defined as a restoring force in a material caused by a deformation divided by an area over which the restoring force is applied. Strain may be defined as a ratio of a change in a mechanical dimension of a material caused by stress with respect to an original state of the material.

A longitudinal modulus M (also known as a P-wave modulus or a constrained modulus) is used to describe isotropic homogeneous materials. The longitudinal modulus M is defined as a ratio of axial stress to axial strain in a uniaxial strain state where all other non-axial strains are zero, a state also referred to as zero lateral strain.

Young's modulus E (also referred to simply as an elastic modulus) is used to describe tensile elasticity. Tensile elasticity of a material is an axial deformation response when opposing forces are applied along an axis. Young's modulus E is defined as a ratio of tensile stress to tensile strain.

Lamé's first parameter $\lambda_{Lamé}$ (Greek: lambda-Lamé is also used to describe tensile elasticity.

A shear modulus G (also known as modulus of rigidity, μ, Greek: mu, or Lamé's second parameter) is used to describe a shear deformation response of a material at constant volume when opposing forces are applied. The shear modulus G is defined as shear stress over shear strain and may be used to derive a viscosity of the material.

A bulk modulus K is used to describe a volumetric elasticity or an isotropic deformation response of a material to an isotropic force, such as gas pressure. The bulk modulus K is defined as volumetric stress over volumetric strain or as the inverse of compressibility κ (Greek: kappa), The bulk modulus K is an extension of Young's modulus E to three dimensions.

Poisson's ratio ν (Greek: nu, also known as Poisson's number) is used to describe a deformation response of a material, when compressed along a first axis, to expand in a second axis and a third axis both perpendicular to the first axis. Poisson's ratio ν is defined as a negative ratio of transverse strain to axial strain or as a fraction of expansion divided by a fraction of compression.

For a homogeneous isotropic linear elastic material, certain equations are used to describe relationships among the various moduli described above. For example, the bulk modulus K, Young's modulus E, and the shear modulus G are related to Poisson's ratio ν, as given in Equation 1.

$$\upsilon = \frac{E}{2G} - 1 = \frac{3K - E}{6K} = \frac{3K - 2G}{6K + 2G} \qquad \text{Equation 1}$$

Also, the bulk modulus K, the shear modulus G, and the longitudinal modulus are related as given in Equation 2.

$$M = K + \frac{4G}{3} \qquad \text{Equation 2}$$

As noted previously, Brillouin scattering may be employed to measure a biomechanical property of eye tissue. In Brillouin scattering, an acoustic wave, also referred to as a phonon, may indicate position dependent mass density variations inside a material. Because of localized compressions resulting from the mass density variation, an optical density of the material, also known as an index of refraction, may vary locally. The local variations in optical density n may result in a spatially periodic optical density variation, which behaves as a diffraction element for coherent light incident on the material. Brillouin scattering occurs when the coherent light interacts with such a diffraction element by being deflected or reflected from the material. Because the phonon is traveling within the material at a given velocity, light deflected or reflected from the phonon is subjected to a Doppler shift in frequency (or wavelength). In other words, the Brillouin scattered photons will have a different energy than the incident photons due to an inelastic scattering process. The change in the photon energy may be expressed as a change in frequency f (or wavelength λ), which are given in Equation 3.

$$f\lambda = \frac{c}{n} \qquad \text{Equation 3}$$

In Equation 3, c is the speed of light in vacuum and n is the optical density of the undisturbed material. The Brillouin scattering results in a frequency shift $f_B$ (or a wavelength shift $\lambda_B$) that may be positive or negative with respect to the frequency f (or the wavelength $\lambda$) of the incident photon. Consequently, an in elastically Brillouin-scattered photon will have possible frequencies given by $f=f_B$ (or possible wavelengths given by $\lambda \pm \lambda_B$). A spectrum of the Brillouin scattered light will include elastically deflected or reflected light, forming a Rayleigh peak at frequency f (or wavelength $\lambda$), along with the in elastically Brillouin-scattered light, forming at least one additional side peak (also referred to as a side band). When the side peak results from a scattered photon with higher energy than the incident photon, a Stokes peak at $f+f_B$ (or at $\lambda-\lambda_B$) may be observed. When the side peak results from a scattered photon with lower energy than the incident photon, an anti-Stokes peak at $f-f_B$ (or at $\lambda+\lambda_B$) may be observed.

In general, Brillouin-scattered photons will change propagation direction, such that the frequency shift $f_B$ of the Brillouin-scattered light depends on a scattering angle $\theta$ between the incident photon and the Brillouin-scattered photon, as given in Equation 4.

$$f_B = \pm \frac{2nV}{\lambda} \cos(\theta/2) \qquad \text{Equation 4}$$

In Equation 4, n is the optical density of the undisturbed material, V is the velocity of the phonon in the material, $\lambda$ is the wavelength of the incident photon in vacuum, and $\theta$ is the scattering angle. Per definition, the propagation direction of the incident photon is anti-parallel to the propagation direction of the Brillouin-scattered photon when $\theta$ is zero such that the incident photon is normal to a surface of the material. In Equation 4, the positive (+) result corresponds to the anti-Stokes Brillouin peak, while the negative result (−) corresponds to the Stokes Brillouin peak. For wavelengths $|\lambda_B| \ll \lambda$, Equation 5 describes the relationship between $f_B$ and $\lambda_B$ $$|f_B| \approx \frac{|\lambda_B|}{\lambda^2} \qquad \text{Equation 5}$$

Because the frequency shift $f_B$ depends on the scattering angle $\theta$, each scattering angle $\theta$ is associated with a specific frequency shift $f_B$. A maximum or minimum value of the frequency shift is obtained by setting $\theta=0°$ in Equation 3, resulting in Equation 6, which corresponds to a normal incident light beam on the Brillouin scattering material.

$$f_B = \pm \frac{2nV}{\lambda} \qquad \text{Equation 6}$$

In the special case of $\theta=0°$, the frequency shift $f_B$ may be referred to as a longitudinal Brillouin shift.

By spectroscopically analyzing the Brillouin scattered light beam, certain biomechanical properties of the scattering material may be determined. For example, a complex valued longitudinal modulus M depends on the velocity of the phonon V as given by Equation 7.

$$M = M_1 + iM_2 = \rho V^2 + i\rho V^2 \left[\frac{\Delta f_B}{f_B}\right] \qquad \text{Equation 7}$$

In Equation 7, $\rho$ is a mass density of the material in which the phonon propagates, and $\Delta f_B$ is the line width of the Brillouin scattering side band.

The line width $\Delta f_B$ corresponds to the reciprocal of a lifetime of the phonon and characterizes the attenuation of the phonon (sound wave) during propagation through the material. In one embodiment, the line width $\Delta f_B$ may be measured as the full width at half maximum (FWHM) of the Stokes or anti-Stokes Brillouin peak. In other embodiments, another suitable definition of a spectral width that characterizes the frequency interval $\Delta f_B$ may be used. For example, an amplitude of all spectral components may be assumed to be equal to or greater than a specified fraction of a spectral component having a maximum amplitude.

When the Brillouin scattered photon emerges in the anti-parallel direction to the incident photon, such as when $\theta=0°$, the shear modulus G will be zero and the longitudinal modulus M will equal the bulk modulus, as is evident from Equation 2. In this case, the values $M_1$ and $M_2$ for the complex valued longitudinal modulus M will be respectively given by Equations 8 and 9.

$$M_1 = \frac{\lambda^2 \rho}{4n^2} f_B^2 \qquad \text{Equation 8}$$

$$M_2 = \frac{\lambda^2 \rho}{4n^2} f_B \Delta f_B \qquad \text{Equation 9}$$

In Equation 8, $M_1$ describes an elastomechanical property of the material, while in Equation 9, $M_2$ describes a viscoelastic property of the material. Accordingly, by measuring the frequency shift $f_B$ of one of the side bands (either Stokes or anti-Stokes) of a Brillouin scattered light beam backscattered from a material (also referred to as a Brillouin signal beam) in response to an incident beam (also referred to as a Brillouin sample beam), an elastomechanical property of the material may be determined. Furthermore, by also measuring the line width $\Delta f_B$ of the side band, a viscoelastic property of the material may be determined.

In addition to Brillouin scattering. SHG signals from human cornea have been associated with the position and distribution of the fibrils in the cornea. SHG refers to second order nonlinear emission of photons at half-wavelength by a material in response to excitation at full-wavelength, as given by Equation 10.

$$\lambda_{SHG} = \lambda_{I/2} \qquad \text{Equation 10}$$

In Equation 10, $\lambda_{SHG}$ is the wavelength of the SHG signal in a SHG signal beam and $\lambda_I$ is the wavelength of the excitation beam (also referred to as a SHG sample beam).

The excitation for SHG signals from human cornea may be performed using a fs-fiber laser focused at a desired sampling location for precise spatial collection of SHG signals that can be used to generate images of conical biostructures. In some embodiments, the excitation area may be on the order of a few microns when collecting SHG signals from human cornea. Fibrils in the cornea are comprised of collagen, which is known to be a highly effective nonlinear SHG signal source. Furthermore, the nonlinear interaction of the excitation beam with corneal collagen fibrils is dependent on the position, orientation, density, and alignment of the collagen fibrils, which may result in the SHG signal providing significant insight into the biostructural condition of various corneal tissues.

For in vivo imaging, backward SHG signals (B-SHG) may be obtained from human cornea. The B-SHG signal beam may be emitted in a roughly anti-parallel direction to the incident SHG sample beam and may be detected by any suitable optical detection system. In some embodiments, a photomultiplier tube (PMT) may be used as an SHG detector for high sensitivity applications of imaging using B-SHG signals. In some embodiments, a multi-channel plate detector, which is similar to a PMT but provides further spatial resolution using a plurality of separate channels, may be used as the SHG detector. The SHG detector may be equipped with an optical filter to discriminate the $\lambda_{SHG}$ wavelength from the measurement beam returning from the sampled material. When a PMT or similar photodetector is used, a photocathode material may be selected for a desired sensitivity to the $\lambda_{SHG}$ wavelength. Furthermore, in some instances, polarization of the SHG sample beam may be employed for additional selectivity to particular emission modes of the sampled material. The polarization-sensitive emission modes may be related to morphological features of collagen fibrils when the sampled material is human corneal tissue. When the SHG sample beam is polarized, the SHG detector may also include a polarization filter to discriminate various polarization orientations in the SHG signal beam.

Referring now to the drawings, FIG. 1 is a block diagram showing an optical instrument 100 for biomechanical diagnosis of eye disease. Optical instrument 100 is not drawn to scale but is a schematic representation. As shown, optical instrument 100 is used to analyze sample 112, which may represent a human eye, and in particular, to analyze a cornea 114 of the human eye. Also, in optical instrument 100, coordinate system 120 defines an axial direction in Z and lateral directions in X and Y, which are relative to sample 112 such that SHG sample beam 130 and Brillouin sample beam 131 propagate towards sample 112 in the axial direction Z. Optical instrument 100 accordingly enables simultaneous capture of both Brillouin signals and SHG signals from sample 112 using a measurement process that is spatially correlated. In this manner, optical instrument 100 may enable improved analysis and measurement of certain physical properties of eye tissue in sample 112 in many diagnostic and clinical applications.

As shown, optical instrument 100 includes SHG source 102 from which SHG sample beam 130 is generated. When SHG source 102 is a fs-fiber laser, the $\lambda_f$ wavelength may be 1030 nanometers) in particular embodiments, and the $\lambda_{SHG}$ wavelength may correspondingly be 515 nm. Optical instrument 100 further includes Brillouin source 104 from which Brillouin sample beam 132 is generated. Brillouin source 104 may be any narrowband light source suitable for Brillouin scattering in eye tissue. In some embodiments, Brillouin source 104 is a single mode continuous wave laser having a wavelength of 532 nm and a line width of about 1 MHz. SHG source 102 and Brillouin source 104 may be positioned to be confocal with respect to sample 112 at focus position 116, which may be adjusted using focusing lens 124.

In FIG. 1, SHG sample beam 130 and Brillouin sample beam 132 are combined into a single optical path at partial mirror 110-1. The combined beam of SHG sample beam 130 and Brillouin sample beam 132 may be spatially modulated in the X-Y plane using scanner 118, in order to scan various locations in sample 112. Scanner 118 may accordingly modulate focus position 116 in the X-Y plane to sample various locations in sample 112, such as different areas of interest in cornea 114, From scanner 118, the combined beam of SHG sample beam 130 and Brillouin sample beam 132 may propagate to sample 112 at partial mirror 110-2, via focusing lens 124. Focusing lens 124 may be adjustable in the Z axis using any suitable mechanism to vary a focus position 116 along the Z axis. Thus, in the embodiment shown in FIG. 1, SHG sample beam 130 and Brillouin sample beam 132 are propagated to sample 112 along a common optical path from partial mirror 110-1, which serves as a common optical start point for both SHG sample beam 130 and Brillouin sample beam 132.

From partial mirror 110-2 towards sample 112, the combined beam of SHG sample beam 130 and Brillouin sample beam 132 may propagate to sample 112 in a normal or substantially normal direction to a surface of sample 112. To the extent that the combined beam has a certain beam width, focusing lens 124 may bundle SHG sample beam 130 and Brillouin sample beam 132 to a desired sample area at focus position 116. Then, a combined beam of SHG signal beam 131 and Brillouin signal beam 133 may be scattered back from sample 112 towards partial mirror 110-2. It is noted that the sampling geometry depicted in optical instrument 100 is exemplary and may be modified in different embodiments.

From partial mirror 110-2 towards partial mirror 110-3, the combined beam of SHG signal beam 131 and Brillouin signal beam 133 may propagate through aperture 122. Aperture 122 may be confocally arranged with respect to SHG signal beam 131 and Brillouin signal beam 133. Aperture 122 may be used to limit photons in SHG signal beam 131 and Brillouin signal beam 133 to a particular scan angle, for example, depending on scanner 118. Accordingly, aperture 122 may be mechanically adjustable depending on a scan angle used by scanner 118. In other embodiments, focusing lens 124 may be used to center or align SHG sample beam 130 and Brillouin sample beam 132, such that SHG signal beam 131 and Brillouin signal beam 133 are aligned with aperture 122, for example, when aperture 122 is fixed.

At partial mirror 110-3, SHG signal beam 131 may be directed to SHG detector 106 via detection lens 126, while Brillouin signal beam 133 may be directed to Brillouin detector 108 via detection lens 128. Both detection lenses 126 and 128 may be arranged confocally with respect to SHG signal beam 131 and Brillouin signal beam 133. SHG detector 106 may be any suitable detector for SHG signal beam 131, such as a PMT or a multi-channel plate detector, as described above.

Brillouin detector 108 may include a high-resolution spectrometer suitable for discriminating Rayleigh scattering from Brillouin scattering. Because the Rayleigh scattered beam may have a significantly greater amplitude than the Brillouin scattered beam and both scattered beams may be relatively close together spectrally, Brillouin detector 108 may have high spectral resolution and also high spectral contrast. In particular embodiments, Brillouin detector 108 may include a charge-coupled device (CCD) array as an optical sensor.

In operation of optical instrument 100, the combined beam of SHG sample beam 130 and Brillouin sample beam 132 may be confocally propagated to focus position 116, which may be modulated in the X-Y plane using scanner 118. Focus position 116 may be modulated in Z using focusing lens 124. In this manner, various points, lines, areas, and volumes in sample 112 may be scanned and analyzed using optical instrument 100.

At focus position 116, Brillouin signal beam 133 may be measured by Brillouin detector 108. Specifically, Brillouin detector 108 may measure the frequency shift $f_B$ of one (or both) of the side bands (either Stokes or anti-Stokes) in Brillouin signal beam 133. Brillouin detector 108 may also measure the line width $\Delta f_B$ of one or both of the side bands. With the measured frequency shift $f_B$ and the measured the line width $\Delta f_B$, an elastomechanical property and a viscoelastic property at focus position 116 may be determined, as explained above with respect to Equations 8 and 9.

Simultaneously and from the same focus position 116, SHG signal beam 131 may be measured by SHG detector 106. Specifically, SHG detector 106 may register a signal amplitude of the wavelength in SHG signal beam 131, In particular, SHG detector 106 may be sensitive to small amplitudes at the $\lambda_{SHG}$ wavelength. Because the signal amplitude of the $\lambda_{SHG}$ wavelength is indicative of a morphological structure of collagen fibrils at focus position 116, the signal amplitude registered by SHG detector 106 may be used to generate certain images of eye tissue in sample 112. The image information generated by SHG detector 106 in this manner may be precisely spatially correlated with the elastomechanical property and the viscoelastic property at focus position 116. The resulting data generated by optical instrument 100 may provide a more complete understanding and analysis of a condition of sample 112 at focus position 116, and enable early biomechanical diagnosis of various eye diseases.

It is noted that, in various embodiments or arrangements of optical instrument 100, different implementations, layouts and diversions of beams may be used. For example, certain portions of optical paths used in optical instrument 100 may include optical fibers. In some embodiments, certain portions of optical paths used in optical instrument 100 may include optical waveguides. Certain portions of optical paths used in optical instrument 100 may represent optical paths within a medium, such as vacuum, free space, a gaseous environment, or the atmosphere. In given embodiments, a polarizing element may be used with at least one of SHG sample beam 130 and Brillouin sample beam 132, and a polarization filter may be used when detecting at least one of SHG signal beam 131 and Brillouin signal beam 133. In another arrangement, scanner 118 may be omitted and another scanning element, such as an objective, may be used. In particular embodiments, at least a portion of the optical components included with optical instrument 100 may be miniaturized and combined into a compact unit having relatively small mass and external dimensions, such that the entire compact unit is held by an external scanning element and moved with respect to sample 112. Also, different orientations of coordinate system 120 may be used in certain embodiments of optical instrument 100.

In various embodiments, optical instrument 100 may be used to characterize or analyze intra-corneal layer biostructures, such as fibrils or microfibrils in human corneal stroma.

It is noted that optical instrument 100 is not drawn to scale but is a schematic representation. Modifications, additions, or omissions may be made to optical instrument 100 without departing from the scope of the disclosure. The components and elements of optical instrument 100, as described herein, may be integrated or separated according to particular applications. Moreover, the operations of optical instrument 100 may be performed by more, fewer, or other components.

Figure 2:
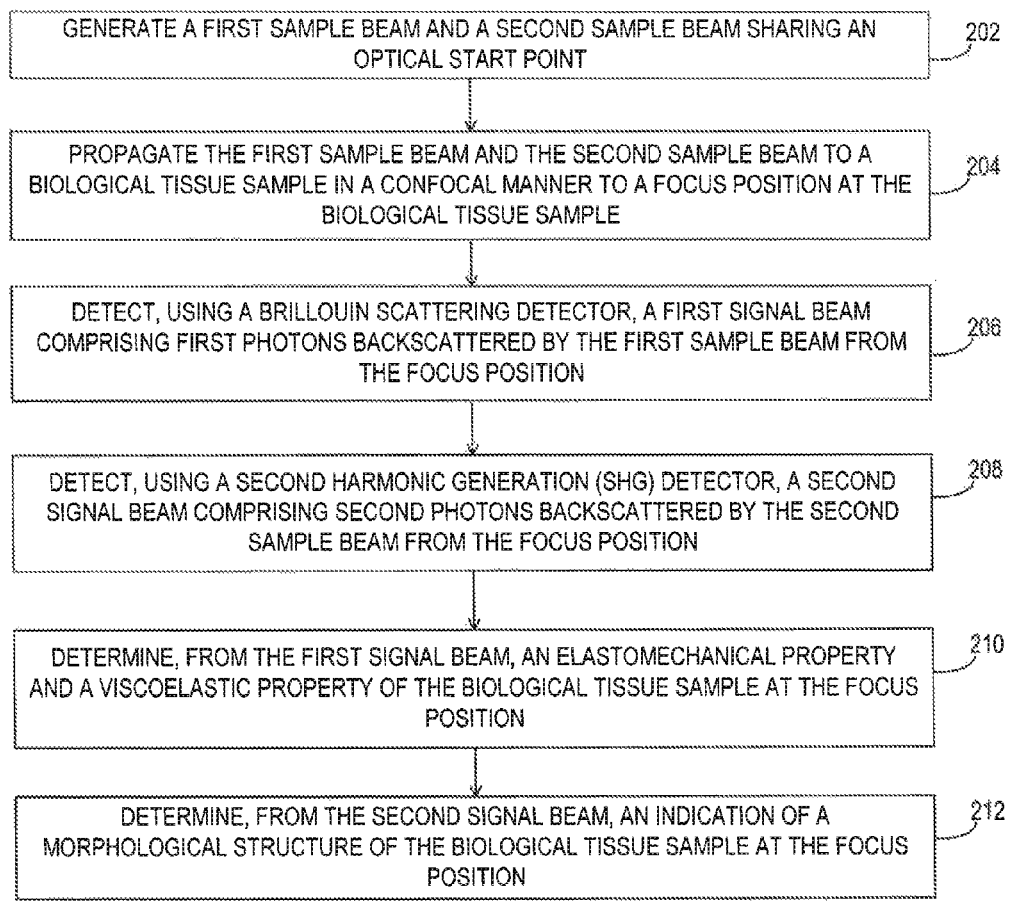
FIG. 2 is a flow chart of selected elements of a method for biomechanical diagnosis of eye disease.

Referring now to FIG. 2, a block diagram of selected elements of an embodiment of a method 200 for performing biomechanical diagnosis of eye disease, as described herein, is depicted in flowchart form. Method 200 may be implemented by optical instrument 100 (see FIG. 1). It is noted that certain operations described in method 200 may be optional or may be rearranged in different embodiments.

Method 200 begins at step 202 by generating a first sample beam and a second sample beam sharing an optical start point. At step 204, the first sample beam and the second sample beam are propagated to a biological tissue sample in a confocal manner to a focus position at the biological tissue sample. At step 206, a first signal beam comprising first photons backscattered by the first sample beam from the focus position is detected using a Brillouin scattering detector. At step 208, a second signal beam comprising second photons backscattered by the second sample beam from the focus position is detected using a second harmonic generation (SHG) detector. At step 210, an elastomechanical property and a viscoelastic property of the biological tissue sample at the focus position is determined from the first signal beam. At step 212, an indication of a morphological structure of the biological tissue sample at the focus position is determined from the second signal beam.

Referring now to FIG. 3, a block diagram of selected elements of an embodiment of a method 300 for performing biomechanical diagnosis of eye disease, as described herein, is depicted in flowchart form. Method 300 may be implemented by optical instrument 100 (see FIG. 1). In particular embodiments, method 300 may include further detail regarding step 204 in method 200. It is noted that certain operations described in method 300 may be optional or may be rearranged in different embodiments.

Method 300 begins at step 302 by varying an axial position of the focus position within the biological tissue sample along a first axis parallel to the first sample beam and the second sample beam. At step 304, a lateral position of the focus position is varied within the biological tissue sample along at least one of a second axis and a third axis that are perpendicular to the first axis. At step 306, the biological tissue sample is scanned to generate image data using the second signal beam, such that both the first sample beam and the second sample beam are directed to different common positions at the biological tissue sample, and including varying at least one of the axial position of the focus position and the lateral position of the focus position.

As disclosed herein, a method and system for performing biomechanical diagnosis of eye disease may include a Brillouin light source to generate a Brillouin sample beam, and a second harmonic generation (SHG) light source to generate an SHG sample beam. Both the Brillouin sample beam and the SHG sample may be coincidentally directed to a biological tissue sample in a confocal manner to a focus position. Brillouin scattering resulting from the Brillouin sample beam may be detected to determine an elastomechanical property and a viscoelastic property of the sample. SHG scattering resulting from the SHG beam may be detected to determine an indication of a morphological structure of the sample. The sample may be an in vivo human cornea.

Method 200 of FIG. 2 and method 300 of FIG. 3 may be performed using a computer programmed to generate or control the location, intensity, or other properties of the sample beams and to process detected signal beams. In some embodiments, such a programmed computer maybe part of optical instrument 100 shown in FIG. 1. In some embodiments, the programmed computer may be connected to optical instrument 100 in a wired or wireless manner to perform at least certain portions of methods 200 or 300. The programmed computer may include special-purpose components, such as components integral with SHG source 102, Brillouin source 104, focusing lens 124, partial mirror 110, scanner 118, SHG detector 106, Brillouin detector 108, and aperture 122. For instance, the programmed computer may include, or may control, one or more switches that change the state of one or more of the above components in response to the signal beams detected. For example, when the signal beams are not in focus, the programmed computer may use one or more switches or otherwise cause a change in the position or size of focusing lens 124, partial mirror 110 or aperture 122. In another example, which is not exclusive of the first example, when the signal beams are not of the correct intensity, the programmed computer may use one or more switches or otherwise cause a change in SHG source 102 or Brillouin source 104.

Processing detected signal beams may include aspects directed to generating or controlling the location, intensity, or other properties of the sample beams and aspects directed to generate information regarding a biomechanical property of the biological tissue sample. For instance, some processing may generate a warning when one or more aspects of the signal beams are not sage. Some processing may generate a visual display reflective of the biomechanical property. Such a display may be generated in real time, or after some delay, particularly when biomechanical properties from different locations in the biological tissue sample are included.

The programmed computer may include more than one computer which may or may not be in communication with one another. For instance, one computer may receive data regarding detected signal beams and use the data to generate or control the location, intensity, or other properties of the sample beams, while a separate computer may received data regarding detected signal beams and use the information to generate information regarding a biomechanical property of the biological tissue sample.

Figure 4:
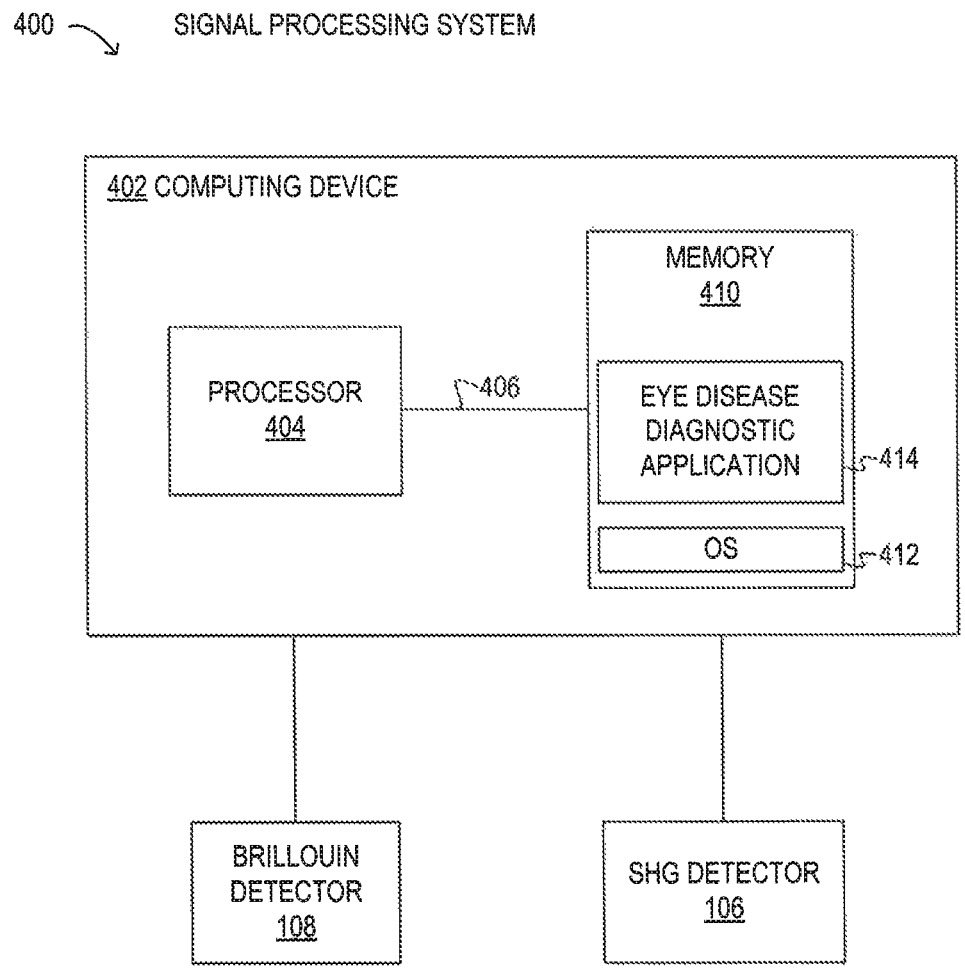
FIG. 4 is a block diagram of selected elements of an embodiment of a signal processing system for biomechanical diagnosis of eye disease.

Referring now to FIG. 4, a block diagram illustrating selected elements of an embodiment of a signal processing system 400 is presented. In the embodiment depicted in FIG. 4, signal processing system 400 includes computing device 402, which is coupled to Brillouin detector 108 and SHG detector 106, while computing device 402 includes processor 404 coupled via shared bus 406 to memory media collectively identified as memory 410. As shown, signal processing system 400 may be included with optical instrument 100 in FIG. 1 for biomechanical diagnosis of eye disease, as disclosed herein.

In various embodiments, computing device 402 may include a network adapter for interfacing to a network. Computing device 402 may include a peripheral adapter to connect to various input and output devices. For example, computing device 402 may communicate with Brillouin detector 108 and SHG detector 106 via an input device to receive output signals for biomechanical diagnosis of eye disease, as described herein. Computing device 402 may also communicate with Brillouin detector 108, SHG detector 106, or other components, via an output device to control various aspects of optical instrument 100.

Memory 410 may represent any of a variety of persistent memory media, volatile memory media, fixed memory media, and removable memory media, among others, Memory 410 may be operable to store instructions, data, or both. As shown, memory 410 stores instructions or code executable by processor 404, namely, an operating system (OS) 412, and an eye disease diagnostic application 414. Operating system 412 may be a UNIX or UNIX-like operating system, a Windows® family operating system, and embedded operating system, or another suitable operating system. Eye disease diagnostic application 414 may represent instructions or code executable by processor 404 to implement at least certain portions of methods 200 and 300 and associated functionality, as described above.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A method for performing biomechanical diagnosis of eye disease, comprising:
   generating a first sample beam and a second sample beam sharing an optical start point;
   propagating the first sample beam and the second sample beam to a biological tissue sample in a confocal manner to a focus position at the biological tissue sample;
   detecting, using a Brillouin scattering detector, a first signal beam comprising first photons backscattered by the first sample beam from the focus position; and
   detecting, using a second harmonic generation (SHG) detector, a second signal beam comprising second photons backscattered by the second sample beam from the focus position.

2. The method of claim 1, wherein propagating the first sample beam and the second sample beam to the sample in the confocal manner includes propagating the first sample beam and the second sample beam along a common optical path.

3. The method of claim 1, wherein:
   the first sample beam is generated using a narrow band continuous wave laser;
   the second sample beam is generated using a femtosecond-fiber laser;
   the Brillouin scattering detector includes a spectrometer; and
   the SHG detector includes a photocathode sensitive to the second signal beam.

4. The method of claim 1, wherein the first signal beam includes Rayleigh scattered photons and Brillouin scattered photons from the focus position, and the second signal beam includes photons at a half-wavelength of a wavelength of the second sample beam.

5. The method of claim 1, wherein the biological tissue sample is in vivo biological tissue comprising a portion of a human eye.

6. The method of claim 1, further comprising:
   determining, from the first signal beam, an elastomechanical property of the biological tissue sample at the focus position;
   determining, from the first signal beam, a viscoelastic property of the biological tissue sample at the focus position; and
   determining, from the second signal beam, an indication of a morphological structure of the biological tissue sample at the focus position.

7. The method of claim 1, wherein propagating the first sample beam and the second sample beam to the sample in the confocal manner includes:
   varying an axial position of the focus position within the biological tissue sample along a first axis parallel to the first sample beam and the second sample beam.

8. The method of claim 7, wherein propagating the first sample beam and the second sample beam to the sample in the confocal manner includes:
   varying a lateral position of the focus position within the biological tissue sample along at least one of a second axis and a third axis that are perpendicular to the first axis.

9. The method of claim 8, wherein propagating the first sample beam and the second sample beam to the sample in the confocal manner includes:

scanning the biological tissue sample to generate image data using the second signal beam, wherein both the first sample beam and the second sample beam are directed to different common positions at the biological tissue sample, wherein the scanning comprises varying at least one of the axial position of the focus position and the lateral position of the focus position.

10. An optical instrument for performing biomechanical diagnosis of eye disease, comprising:

a first light source to generate a first sample beam;

a second light source to generate a second sample beam;

a first partial mirror to superimpose the first sample beam and the second sample beam to generate a combined sample beam;

a Brillouin scattering detector including a spectrometer to receive a first signal beam comprising first photons backscattered by the first sample beam from a focus position at a biological tissue sample; and a second harmonic generation (SHG) detector including a photocathode sensitive to a second signal beam comprising second photons backscattered by the second sample beam from the focus position.

11. The optical instrument of claim 10, further comprising a second partial mirror to:

propagate the combined sample beam to the focus position in a confocal manner; and propagate a combined signal beam comprising the first signal beam and the second signal beam from the focus position in a confocal manner.

12. The optical instrument of claim 10, further comprising:

a focusing element to vary an axial position of the focus position at the biological tissue sample in a confocal manner along a first axis parallel to the combined sample beam.

13. The optical instrument of claim 12, further comprising:

a scanning element to vary a lateral position of the focus position at the biological tissue sample in a confocal manner along at least one of a second axis and a third axis that are perpendicular to the first axis.

14. The optical instrument of claim 13, wherein at least one of the focusing element and the scanning element are to:

scan the biological tissue sample to generate image data using the second signal beam, wherein both the first sample beam and the second sample beam are directed to different common positions at the biological tissue sample, including varying at least one of the axial position of the focus position and the lateral position of the focus position.

15. The optical instrument of claim 10, wherein:

the first light source comprises a narrow band continuous wave laser;

the second light source comprises a femtosecond-fiber laser;

the Brillouin scattering detector includes a spectrometer; and the SHG detector includes a photocathode sensitive to the second signal beam.

16. The optical instrument of claim 10, wherein the first signal beam includes Rayleigh scattered photons and Brillouin scattered photons from the focus position, and the second signal beam includes photons at a half-wavelength of a wavelength of the second sample beam.

17. The optical instrument of claim 10, wherein the biological tissue sample is in vivo biological tissue comprising a portion of a human eye.

18. The optical instrument of claim 10, wherein:

the Brillouin scattering detector is to:

determine, from the first signal beam, an elastomechanical property of the biological tissue at the focus position; and determine, from the first signal beam, a viscoelastic property of the biological tissue at the focus position; and the SHG detector is to determine, from the second signal beam, an indication of a morphological structure of the biological tissue sample at the focus position.

* * * * *